US011946885B2

(12) United States Patent
Yu et al.

(10) Patent No.: US 11,946,885 B2
(45) Date of Patent: Apr. 2, 2024

(54) NONINVASIVE QUANTITATION OF FULL VERSUS EMPTY CAPSIDS USING WATER PROTON NMR

(71) Applicant: UNIVERSITY OF MARYLAND, BALTIMORE, Baltimore, MD (US)

(72) Inventors: Yihua (Bruce) Yu, Ellicott City, MD (US); Marc Taraban, North Potomac, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 17 days.

(21) Appl. No.: 17/842,990

(22) Filed: Jun. 17, 2022

(65) Prior Publication Data
US 2022/0317073 A1   Oct. 6, 2022

Related U.S. Application Data

(63) Continuation of application No. PCT/US2020/065803, filed on Dec. 18, 2020.

(60) Provisional application No. 62/951,128, filed on Dec. 20, 2019.

(51) Int. Cl.
G01N 24/08 (2006.01)
C12N 15/86 (2006.01)
G01R 33/44 (2006.01)

(52) U.S. Cl.
CPC ............ G01N 24/08 (2013.01); C12N 15/86 (2013.01); G01R 33/448 (2013.01); C12N 2750/14143 (2013.01)

(58) Field of Classification Search
CPC .......... C12N 2750/14143; C12N 15/86; G01R 33/448; G01N 24/08
See application file for complete search history.

(56) References Cited

U.S. PATENT DOCUMENTS

| 5,492,814 | A | 2/1996 | Weissleder |
|---|---|---|---|
| 10,267,754 | B2 | 4/2019 | Yu et al. |
| 10,514,347 | B2 | 12/2019 | Yu et al. |
| 10,724,974 | B2 | 7/2020 | Yu et al. |
| 11,119,061 | B2 | 9/2021 | Yu et al. |

(Continued)

FOREIGN PATENT DOCUMENTS

| WO | WO 2019/212922 | 11/2019 |
|---|---|---|
| WO | WO 2020/185828 | 9/2020 |

OTHER PUBLICATIONS

Baroni et al. "Relaxometric Characterization of Balsamic Vinegar." meeting abstract 6th Conference on Field Cycling NMR Relaxometry Turin (Italy) Jun. 4, 2009. p. 73.

(Continued)

Primary Examiner — Gregory H Curran
(74) Attorney, Agent, or Firm — Casimir Jones, SC; Tristan A. Fuierer

(57) ABSTRACT

A method of using the relaxation rate ($R_1$ and/or $R_2$) of solvent NMR signal to noninvasively assess whether viral capsids in a capsid preparation are full or empty, and the percentage of full capsids if the vial contains a mixture of full and empty capsids. The method can simply, rapidly, and non-invasively prove the safety and potency of the capsid preparation and thus whether the capsid preparation can be approved for clinical use, without requiring any sample preparation or reagent addition.

21 Claims, 4 Drawing Sheets

(56) References Cited

U.S. PATENT DOCUMENTS

| | | | |
|---|---|---|---|
| 11,345,929 B2* | 5/2022 | Wang | G01N 33/6803 |
| 11,346,908 B2 | 5/2022 | Yu et al. | |
| 11,725,192 B2* | 8/2023 | Khatwani | B01D 15/166 |
| | | | 435/239 |
| 2005/0287527 A1 | 12/2005 | Ni et al. | |
| 2006/0269965 A1 | 11/2006 | Josephson et al. | |
| 2007/0116602 A1 | 5/2007 | Lee | |
| 2010/0072994 A1 | 3/2010 | Lee et al. | |
| 2012/0100546 A1 | 4/2012 | Lowery, Jr. et al. | |
| 2012/0164644 A1 | 6/2012 | Neely et al. | |
| 2013/0057279 A1 | 3/2013 | Yu et al. | |
| 2013/0244238 A1 | 9/2013 | Neely et al. | |
| 2013/0265054 A1 | 10/2013 | Lowery, Jr. et al. | |
| 2015/0132231 A1 | 5/2015 | Ko et al. | |
| 2020/0010962 A1 | 1/2020 | Lin | |
| 2020/0110046 A1 | 4/2020 | Yu et al. | |
| 2022/0163468 A1 | 5/2022 | Yu et al. | |

OTHER PUBLICATIONS

Bloembergen et al., Relaxation Effects in Nuclear Magnetic Resonance Absorption. Phys. Rev. 1948, 73, 679-712.

Bouchoux et al., Molecular mobility in dense protein systems: an investigation through 1H NMR relaxometry and diffusometry. J Phys Chem B. Sep. 27, 2012;116(38):11744-53.

Briggs et al., Water proton NMR detection of amid hydrolysis and diglycine dimerization. Chem. Commun., 2018, 54, 7003-7006.

Dalvit et al., High-Throughput NMR-Based Screening with Competition Binding Experiments. J. Am. Chem. Soc 2002, 124, 7702-7709.

Daskiewicz et al. Proton Magnetic Relaxation and Protein Hydration. Nature, 1963; 200(4910): 1006-1007.

Fanali et al., Human serum albumin: from bench to bedside. Mol Aspects Med Jun. 2012;33(3):209-90.

Feng et al., Linear dependency of NMR relaxation rates on shear modulus in hydrogels. Soft Matter, 2011, 7, 9890-9893.

Feng et al., Water proton NMR—a sensitive probe for solute association. Chem. Commun., 2015, 51, 6804-6807.

International Search Report and Written Opinion for PCT/US20/65803, dated Mar. 8, 2021. 8 pages.

Korzhnev et al., Probing Invisible, Low-Populated States of Protein Molecules by Relaxation Dispersion NMR Spectroscopy: An Application to Protein Folding. Acc. Chem. Res., 2008, 41(3), 442-451.

Mao et al., Understanding Radiation Damping in a Simple Way. Concepts Magn. Reson. 1997; 9: 173-187.

Metz et al., Benchtop-NMR and Mri—A new analytical tool in drug delivery research. Int. J. Pharm. 2008, 364, 170-175.

Taraban et al., Assessing Aluminum Vaccine Adjuvant Filling, Sedimentation, and Resuspension in Sealed Vials using Water Prtoton NMR. Spectroscopy. American Pharmaceutical Review. Jan./Feb. 2019. 4 pages.

Taraban et al., Flow Water Proton NMR: In-Line Process Analytical Technology for Continuous Biomanufacturing. Anal. Chem. 2019, 91, 13538-13546.

Taraban et al., Noninvasive detection of nanoparticle clustering by water proton NMR. Transl. Mater. Res. 2017, 4, 025002. 9 pages.

Taraban et al., Rapid and noninvasive Quantification of Capsid Gene Filling Level Using Water Proton Nuclear Magnetic Resonance. Anal. Chem. 2021, 93, 15816-15820.

Taraban et al., Water Flow-NMR—A prospective Contact-Free In-Line Analytical Tool for Continuous Biomanufacturing. PANIC 2019 Conference. 1 page.

Taraban et al., Water Proton NMR for In Situ Detection of Insulin Aggregates. Journal of Pharmaceutical Sciences, 2015, vol. 104, 4132-4141.

Taraban et al., Water Proton NMR: A Tool for Protein Aggregation Characterization. Anal. Chem. 2017, 89, 5494-5502.

Yu et al., Water Proton NMR for Noninvasive Chemical Analysis and Drug Product Inspeciton. American Pharmaceutical Review. 2017. 6 pages.

Iwai et al., NMR solution structure of the monomeric form of the bacteriophage lambda capsid stabilizing protein gpD. Journal of Biomolecular NMR, vol. 31, No. 4, Apr. 1, 2005, pp. 351-356.

Supplementary Extended EP Search Report for EP20903982.5, dated Jan. 31, 2024, 3 pages.

* cited by examiner

NONINVASIVE QUANTITATION OF FULL VERSUS EMPTY CAPSIDS USING WATER PROTON NMR

CROSS REFERENCE TO RELATED APPLICATIONS

This application is filed under the provisions of 35 U.S.C. § 120 and is a continuation-in-part of International Patent Application No. PCT/US2020/065803, filed on Dec. 18, 2020, which claims priority to U.S. Provisional Patent Application No. 62/951,128 filed on Dec. 20, 2019 in the name of Yihua (Bruce) Y U et al. and entitled "Noninvasive Quantitation of Full Versus Empty Capsids Using Water Proton NMR," which are hereby incorporated by reference herein in their entirety.

FIELD

The present invention relates to methods for quality control of preparations comprising viral capsids using solvent nuclear magnetic resonance (NMR). The methods can be used to determine whether the capsid preparations contain an unacceptably high percentage of empty capsids and should not be distributed or used. The methods can be also applied as an analytical technique for in-process quality control and during process development.

DESCRIPTION OF THE RELATED ART

Gene therapy uses capsids (hollow nanoparticles assembled from protein units) to encapsulate nucleic acids for gene delivery. Distinguishing full and empty capsids and assessing the fraction of full capsids in a mixture of full and empty capsids is critically important for gene therapy products.

All current methods for assessing the fraction of full capsids in a capsid-containing sample are invasive and time consuming. The industry gold standard analytical method is analytical ultracentrifugation (AUC). Other techniques include high-performance liquid chromatography (HPLC) with detection at 260 nm and 280 nm (respective maximum absorbance wavelengths of nucleic acids and proteins), cryo-EM with attempt of visually counting empty versus full capsids, laser interferometry, and qPCR to quantify the presence of nucleic acids. All these techniques are invasive, require expensive instruments with large footprints, have low throughput, and none can be performed bench-to-bedside. Moreover, measurement error is typically ±15-20%.

There is a need for a fast and reliable technique which can be used to non-invasively distinguish and quantitate full and empty capsids. Towards that end, the present invention relates to a method of using the transverse relaxation rate of a solvent NMR signal, e.g., $R_2(^1H_2O)$ if the solvent is water, or the longitudinal relaxation rate of a solvent NMR signal, e.g., $R_1(^1H_2O)$ if the solvent is water, to determine whether viral capsids are full or empty as well as to quantitate the capsid content in capsid preparations. Advantageously, the method can be performed noninvasively, without the requirement of opening the vial and/or without destruction of the valuable preparations contained therein.

SUMMARY

The present invention generally relates to a method of using NMR relaxation rates, such as the longitudinal relaxation rate constant $R_1$ and transverse relaxation rate constant $R_2$, preferably the transverse relaxation rate constant $R_2(^1H_2O)$ of water, to assess whether the viral capsids contained in capsid preparations are empty or full as well as to quantitate the capsid content of the capsid preparations.

In one aspect, a method of determining if a capsid preparation comprises full or empty viral capsids is described, said method comprising:
measuring the transverse relaxation rate of solvent $R_{2,m}$ in the capsid preparation; and
determining if the capsid preparation comprises full and/or empty viral capsids by comparing the measured $R_{2,m}$ to reference transverse relaxation rates of solvent $R_{2,r}$, wherein the full viral capsids and the empty viral capsids each have a unique reference $R_{2,r}$ value.

In another aspect, a method of determining capsid content of a capsid preparation is described, said method comprising measuring the transverse relaxation rate of solvent $R_{2,m}$ in the capsid preparation, and calculating the capsid content of the capsid preparation from a standard calibration curve created using the $R_2$ relative to known capsid contents for said capsid preparation.

In another aspect, a method of determining if a capsid preparation has experienced stress-induced damage selected from the group consisting of temperature excursions, a freeze/thaw process, light, agitation, and any combination thereof, said method comprising:
measuring the transverse relaxation rate of solvent $R_{2,m}$ in the capsid preparation; and
determining if the capsid preparation has experienced stress-induced damage by comparing the measured $R_{2,m}$ to a reference transverse relaxation rate of solvent $R_{2,r}$, wherein the reference $R_{2,r}$ represents an acceptable range for the capsid preparation,
wherein when the measured $R_{2,m}$ is inside the reference $R_{2,r}$ range, the capsid preparation has not experienced substantial stress-induced damage and can be used or distributed.

Other aspects, features and advantages of the invention will be more fully apparent from the ensuing disclosure and appended claims.

DETAILED DESCRIPTION, AND PREFERRED EMBODIMENTS THEREOF

Figure 1:
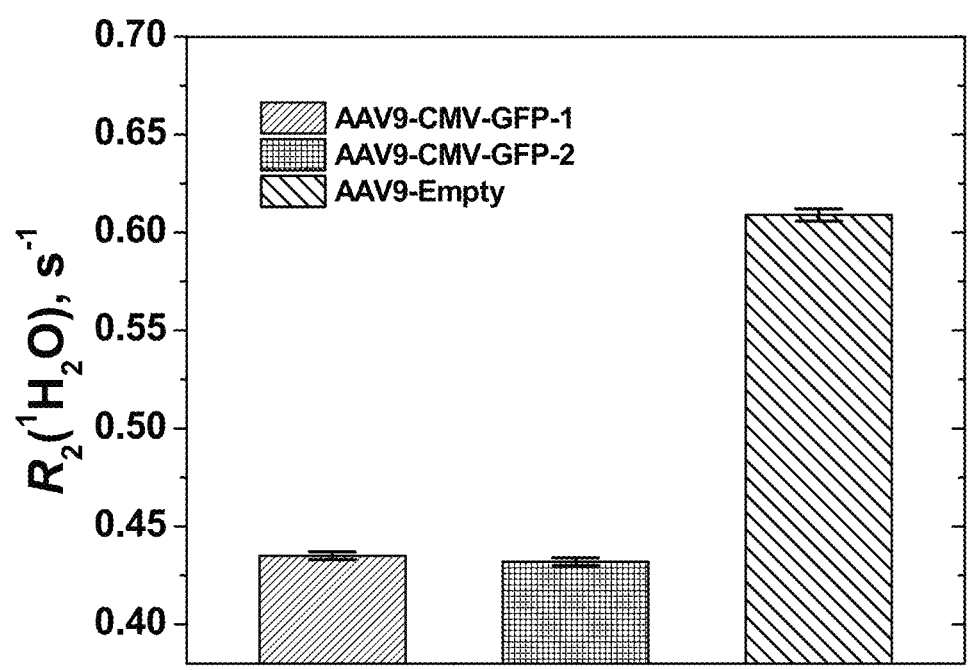
FIG. 1 shows the differences in water proton transverse relaxation rates, $R_2(^1H_2O)$, observed for empty and full capsids for two full capsid samples (AAV9-CMV-GFP-1 and AVV9-CMV-GFP-2) and one empty capsid sample (AAV9-Empty). Error bars (±0.002-0.003 s$^{-1}$) represent the SD of the averages of three consecutive measurements.

The present invention generally relates to a method of using NMR relaxation times or rates of solvent molecules, e.g., water, to non-invasively distinguish and quantitate full and empty capsids that may be present in capsid preparations. In some embodiments, the present invention relates to a method of using NMR relaxation rates (e.g., longitudinal and transverse relaxation rate constants, $R_1$ and $R_2$, respectively) of water molecules to non-invasively distinguish and quantitate full and empty capsids that may be present in capsid preparations. In some embodiments, the present invention relates to a method of using NMR relaxation rates (e.g., longitudinal and transverse relaxation rate constants, $R_1$ and $R_2$, respectively) of water molecules to non-invasively distinguish and quantitate full and empty shells in a shell preparation, wherein the shell preparation comprises shell/core structures Y that can encapsulate material X inside the shell, wherein X can be nucleic acids such as DNA or RNA and Y can be a protein capsid, a lipid nanoparticle (LNP), or a polymer (e.g., a biodegradable cationic polymer). In one embodiment, the shell preparation is an aqueous solution.

In recent years, viral capsids have shown great promise in gene therapy for treating several diseases. Disadvantageously, the development of quality control assays to characterize and certify viral capsids for clinical use has proven to be a challenge. For example, specific assays have to be developed to prove the safety and potency of the capsid preparation, assure the patient's health, and avoid any undesired side effects. Although techniques have been developed, they are invasive, expensive, prone to error and low throughput, and none can be performed bench-to-bedside. In addition, the prior art assays involve the use of reagents and sample manipulation, which pose their own quality control challenges and add additional uncertainty. One advantage of the water NMR (wNMR) measurements described herein is that it requires no additional reagents nor sample manipulation.

During the production of viral capsids, a population of capsids can fail to package the vector genome. These empty capsids can represent up to 90% of the crude harvest for recombinant AAV vector preparations (Dorange, F., et al., Cell GeneTherapy Insights, 2018. 4(2): 119-129; Wright, J. F., et al., Hum Gene Ther, 2009. 20(7): 698-706). The effect of the empty capsids on clinical outcome is not clear, however, it is known that such empty capsids are unable to provide a therapeutic benefit associated with transgene production typical of a full capsid. Moreover, there is a potential for increasing innate or adaptive immune responses to the vector, which then renders empty capsids a concern in gene therapy contexts (Wright, J. F., Molecular Therapy 22: 1-2 (2014)). Knowing this, the accurate and precise quantitation of the "capsid content" (i.e., the percent of full capsids based on the total amount of capsids in the sample) is a valuable characterization tool in viral capsid development and clinical trials of potential gene therapy products, providing information on the safety and potency of the capsid preparation.

As defined herein, a "capsid" or "viral capsid" is a coat or a shell that is composed of a plurality of unit proteins (capsomeres) and surrounds a viral nucleic acid or a core in a virion. The capsid in a drug delivery particle can be selected according to a target organism to which the drug delivery particle is delivered. For example, an animal virus-derived capsid can be used when an animal is the target organism. A plant virus-derived capsid can be used when a plant is the target organism. A bacteriophage-derived capsid can be used when a bacterium is the target organism. The definition of "capsids" and "viral capsids" can also include viral-like particles (VLPs), which can be used as vectors for nucleic acid, antigen, or drug delivery (see, e.g., Hill, B. D. et al., 2018, Curr. Protein Pept. Sci. 19:112; Thong Q. X. et al., 2019, Sci. Rep. 9:3945; Ko, S.-Y. et al., 2019, Sci. Translat. Med. 11:eaav3113), as well as reconstituted capsids (i.e., dissolved lyophilized capsid powder in formulation media).

As defined herein, "nucleic acid" includes, but not limited to, ribonucleic acid, deoxyribonucleic acid, oligoribonucleotide, oligodeoxyribonucleotide, any other oligonucleotide known in the art.

As defined herein, "RNA" or ribonucleic acid includes, but is not limited to, transfer RNA (tRNA), messenger RNA (mRNA), interfering RNA (iRNA), small-interfering RNA (siRNA), and ribosomal RNA (rRNA), and any other RNA molecules and oligonucleotides known in the art.

As defined herein, "DNA" or deoxyribonucleic acid includes, but not limited to, double strand DNA (dsDNA), single strand DNA (ssDNA), coding DNA (cDNA), mitochondrial DNA (mDNA), ribosomal DNA (rDNA) and any other DNA molecules and oligodeoxyribonucleotides known in the art.

As defined herein, a "capsid preparation" or "preparation" corresponds to a composition or solution comprising capsids or viral capsids. The capsid preparation can be a gene therapy product or can be a therapy product or can be a gene product, as readily understood by the person skilled in the art. Any capsid preparation can be evaluated using the methods described herein.

When the capsid is derived from an animal virus, any animal virus included in an RNA virus group or a DNA virus group can be used. Specifically, the capsid may be derived from, for example, any RNA virus that belongs to the family Retroviridae, Picornaviridae, Caliciviridae, Astroviridae, Flaviviridae, Togaviridae, Coronaviridae, Paramyxoviridae, Rhabdoviridae, Filoviridae, Orthomyxoviridae, Bunyaviridae, Arenaviridae, Reoviridae, or Birnaviridae. Alternatively, the capsid may be derived from any DNA virus that belongs to the family Adenoviridae, Herpesviridae, Poxyiridae, Iridoviridae, Hepadnaviridae, Circoviridae, Parvoviridae, or Papovaviridae. A virus belonging to the family Retroviridae in the RNA virus group or a virus belonging to the family Adenoviridae, Parvoviridae, or Herpesviridae in the DNA virus group can be preferably used as the virus from which the capsid is derived. Oncovirus, lentivirus, or spumavirus of the family Retroviridae, adenovirus of the family Adenoviridae, or adeno-associated virus (AAV) of the family Parvoviridae can be particularly preferably used as the virus from which the capsid is derived.

When the capsid is derived from a plant virus, any plant virus included in an RNA virus group or a DNA virus group can also be used. Specifically, the capsid may be derived from, for example, any RNA virus that belongs to the genus *Tenuivirus*, the tobamovirus group, the family Potyviridae, the dianthovirus group, the bromovirus group, the cucumovirus group, the family Rhabdoviridae, the family Reoviridae, or the cryptic virus group. Alternatively, the capsid may be derived from any DNA virus that belongs to the genus *Caulimovirus, Badnavirus*, or *Geminivirus*.

The term "parvovirus" as used herein encompasses the family Parvoviridae, including autonomously replicating parvoviruses and dependoviruses. The autonomous parvoviruses include members of the genera *Parvovirus, Bythrovirus, Densovirus, Iteravirus*, and *Contravirus*. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers).

At present, adeno-associated virus (AAV) vectors are recognized as the gene transfer vectors of choice for therapeutic applications since they have the best safety and efficacy profile for the delivery of genes in vivo. Adeno-associated virus (AAV), a member of the Parvovirus family, is a small nonenveloped, icosahedral virus with single-stranded linear DNA genomes of 4.7 kilobases (kb) to 6 kb. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "AAV" includes AAV type 1 (AAV1), AAV type 2 (AAV2), AAV type 3 (AAV3) (including types 3A and 3B), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10), AAV type 11 (AAV11), avian AAV, bovine AAV, canine AAV, equine AAV, primate AAV, non-primate AAV, ovine AAV, and Clade F AAV and any other AAV serotypes known in the art.

As used herein, the term "empty" with regards to viral capsids (i.e., "empty capsids") refers to those that lack a substantially complete (i.e., "full") vector genome. An "empty capsid" refers to a protein shell that lacks in whole or in part the polynucleotide construct comprising the heterologous nucleotide sequence of interest flanked on both sides by inverted terminal repeats (ITRs). Accordingly, the "empty capsid" does not function to transfer the gene of interest into the host cell. "Empty capsids" can include "incomplete vector DNA," "fragmented vector DNA," or "truncated vector DNA," typical of incomplete encapsidation. Such empty viral capsids are unable to provide a therapeutic benefit typical of a full viral capsid.

As used herein, the term "empty" with regards to the shell/core structures Y, or "empty shell," refers to a shell/core structures Y that comprises a material X, wherein the material X comprises an "incomplete nucleic acid molecule," "fragmented nucleic acid molecule," and/or "truncated nucleic acid molecule," wherein the nucleic acid molecule is the nucleic acid molecule that is intended by the manufacturer to be encapsulated by the shell/core structures Y. The nucleic acid molecule can be double or single stranded.

"Full capsids" are defined herein as an infectious, replication-defective virus including a protein shell, encapsidating a heterologous nucleotide sequence of interest which is flanked on both sides by ITRs. A "full capsid" can transfer the gene of interest into the host cell.

As used herein, the term "full" with regards to the shell/core structures Y, or "full shell," refers to a shell/core structures Y that comprises a material X, wherein the shell is considered to be acceptably filled, as determined by the manufacturer, with the nucleic acid molecule that is intended by the manufacturer to be encapsulated by the shell/core structures Y. Put another way, the "full shells" are substantially devoid of "incomplete nucleic acid molecules," "fragmented nucleic acid molecules," and/or "truncated nucleic acid molecules." "Substantially devoid" is defined herein to mean that less than 5% of the shell/core structures Y in a shell preparation include "incomplete nucleic acid molecules," "fragmented nucleic acid molecules," and/or "truncated nucleic acid molecules," preferably less than 2%, more preferably less than 1%, and most preferably less than 0.1%. The nucleic acid molecule can be double or single stranded.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid nanoparticle" includes a lipid formulation that can be used to deliver a therapeutic nucleic acid (e.g., mRNA or siRNA, or any DNA molecule) to a target site of interest (e.g., cell, tissue, organ, and the like). In one embodiment, the lipid nanoparticle is a nucleic acid-lipid nanoparticle, which is typically formed from a cationic lipid, a non-cationic lipid (e.g., a phospholipid), a conjugated lipid that prevents aggregation of the particle (e.g., a PEG-lipid), and optionally cholesterol. Typically, the lipid nanoparticle has a structure that includes a single monolayer or bilayer of lipids that encapsulates material X (i.e., a nucleic acid) in a solid phase. Unlike liposomes, lipid nanoparticles do not have an aqueous phase or other liquid phase in its interior, but rather the lipids from the bilayer or monolayer shell are directly complexed to the internal material X thereby encapsulating it in a solid core. Lipid nanoparticles are typically spherical vesicles having a relatively uniform dispersion of shape and size, e.g., a diameter in the range of 10 nm to 1000 nm. In the context of nucleic acid delivery, lipid nanoparticles offer many advantages over other lipid-based nucleic acid delivery systems including high nucleic acid encapsulation efficiency, potent transfection, improved penetration into tissues to deliver therapeutics, and low levels of cytotoxicity and immunogenicity. In one embodiment, the lipid nanoparticle encapsulates mRNA.

"Polymers" that can be used as the shell/core structures Y can be non-viral carriers for encapsulating nucleic acids including DNA and RNA, for delivery into cells for therapeutic purposes or for modifying cells. Cationic polymers are suitable for delivering nucleic acids into cells due to their positive charge under physiological conditions for the ease of complexation with nucleic acids and for targeting cells that are typically negatively charged. Polymers can include polyethylene glycol (PEG), polyethylenimine (PEI), polyalkylamine, polyallylamine, polylysine (PLK), polypeptide, chitosan, polysaccharide or polysaccharide functionalized with amino or imino functions, poly(dimethylaminoethyl methacrylate), or co-polymers. Poly(beta-amino ester)s that are biodegradable can also be useful due to their ability to bind DNA, promote cellular uptake, facilitate escape from the endosome, and allow for DNA release in the cytoplasm (Green et al., Acc. Chem. Res. 41:749-759, 2008). Poly (beta-amino ester)s with diamine end-modification can also be used for effective gene delivery (Zugates et al., Mol. Ther. 15:1306-1312, 2007). Some of acrylate-terminated polymers or amine monomer-terminated polymers may also be useful. In one embodiment, the polymer is biodegradable. In one embodiment, the polymer is biodegradable and cationic.

The term "host cell" denotes, for example, microorganisms, yeast cells, insect cells, and mammalian cells, that can be, or have been, used as recipients of a helper construct, a vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As defined herein, a "vial" corresponds to a container, vessel, bottle, syringe, injection pen, or ampoule used to store the viral capsids, wherein the vial comprises glass, plastic, ceramic, rubber, elastomeric material, and/or any non-magnetic metal. The vial can have a screw top, a top that is closed using a cork or plastic stopper, a crimp vial (closed with a rubber stopper and a metal cap), a flip-top or snap cap. The vial can be tubular or have a bottle-like shape with a neck. Other types and shapes of vials used to store particles as well as caps are readily understood by the person skilled in the art. The vials can be optically transparent or not optically transparent. There is no need to peel off any label on the vial, whether the label is transparent or not.

As defined herein, a "non-destructive" measurement is defined as a measurement performed without opening the vial or otherwise accessing, harming, or altering the contents of the vial (for example by withdrawing a portion through a rubber gasket). Alternatively, or in addition to not accessing the contents of a vial, a non-destructive measurement means that no additives or probes or the like (e.g., magnetic particles) are added to the vial prior to the measurement of the longitudinal ($R_1$) or transverse ($R_2$) relaxation rate of solvent, e.g., water, in the vial. Non-destructive also means that there is no need to make the vials optically transparent and no need to peel off any labels on the vials.

Recent breakthrough developments in the instrumentation for nuclear magnetic resonance (NMR) spectroscopy and imaging have opened up opportunities to design novel nondestructive analytical techniques for the nanoparticle industry. Of special importance was the introduction of commercially available, relatively inexpensive benchtop and handheld NMR and magnetic resonance imaging (MRI) instruments and relaxometers (Metz, H., et al. 2008. Int. J. Pharm. 364: 170-178.). Benchtop NMR instruments enable highly accurate measurements of nuclear spin relaxation times $T_1$ and $T_2$. Moreover, most of these instruments have a permanent or electronically cooled magnet with the variable bore from about 10 mm to about 45 mm and even larger which provides a great flexibility in the nonintrusive measurements of vials of various sizes.

Water proton NMR (wNMR) monitors water, which acts as a reporter for analytes dissolved in it. As a reporter, water has many advantages. First, its concentration far surpasses that of any analyte dissolved in it, by $10^3$-$10^6$ fold in most cases. This makes the $^1H_2O$ signal easily detectable by NMR instruments. Further, the solute association can be detected through the solvent NMR signal. In addition, water is "endogenous" to all biomanufacturing processes and all pharmaceutical products, including viral capsids. The high concentration of "endogenous" water makes it possible for wNMR to be performed contact-free in situ.

wNMR is a useful characterization tool for the pharmaceutical industry, thereby allowing the industry to certify viral capsids for release, distribution, and clinical use. For example, wNMR can be used to determine if the viral capsids are empty or full. Further, wNMR can be used to determine the capsid content. With this information, the manufacturer of the viral capsids can determine if the viral capsids can be released, the distributor can determine if the viral capsids can be distributed, and/or pharmacy or healthcare providers can determine if the viral capsids can be administered to patients, e.g., the viral capsids are "full" or have a capsid content above a minimum acceptable capsid content. In addition, because the measurement of the wNMR can be determined easily using benchtop and handheld NMR devices, the end user can also measure the wNMR of the capsid preparation to ensure that the viral capsids remain "full" or have a capsid content above a minimum acceptable capsid content prior to administration, e.g., have not undergone degradation in storage and/or transport. This is particularly advantageous since distribution of the capsid preparation subsequent to manufacturing includes the risk of unacceptable temperature fluctuations (e.g., too hot or too cold), unexpected vibrations, and an unknown length of time between bench and bedside.

The method described herein is a reliable and simple method to assess whether the viral capsids contained in capsid preparations are empty or full as well as quantitate the capsid content. In one embodiment, the method enables the non-destructive assessment of the viral capsids, formulated as aqueous suspensions, without opening the vial or preparation container, without adding any additives, without peeling off the label on the vial, and without relying on sedimentation principles (e.g., AUC). The method described herein is qualitative and quantitative and comprises determining the nuclear spin relaxation rate constant, $R_1(^1H_2O)$ and/or $R_2(^1H_2O)$, of water as a quality control parameter. It is known that empty capsids lack potency and can even lead to deleterious effects if administered to a human or other animal. In the present disclosure, the inventors were able to show that there exists a quantitative variation of the nuclear spin relaxation rate constant, $R_1$ and/or $R_2$, of water between full and empty capsids. Moreover, the capsid content can be easily determined using a calibration curve, as readily understood by the person skilled in the art and discussed hereinafter. Being able to easily and non-invasively determine if capsids are empty, and what percentage are empty, allows the manufacturer, distributor, or administrator of the viral capsids to ensure that capsid preparations comprising an unacceptably high level of empty viral capsids are not released, distributed or administered, respectively. Moreover, the method described herein, which has a low percentage of error and is easy to use, permits the certification of capsid preparations for clinical use. In addition to quality control, the methods described herein can advantageously be used for research purposes including the development and clinical trials of newly developed gene therapy products, where the consistent knowledge of the ratio of empty versus full capsids is of critical importance for the evaluation of efficacy of a gene therapy product.

In one embodiment, the acceptable $R_1(^1H_2O)$ and/or $R_2(^1H_2O)$ constant of the full viral capsids, or preferentially an acceptable range of $R_1(^1H_2O)$ and/or $R_2(^1H_2O)$ constants of said full viral capsids, can be determined by the manufacturer. In one embodiment, the acceptable $R_1(^1H_2O)$ and/or $R_2(^1H_2O)$ constant of the full viral capsids in a vial, or preferentially the acceptable range of $R_1(^1H_2O)$ and/or $R_2(^1H_2O)$ constants of said full viral capsids in the vial, are determined by the manufacturer. The $R_1$ and/or $R_2$ constant (or range of $R_1(^1H_2O)$ and/or $R_2(^1H_2O)$ constants) can be provided in the package insert, on the vial label, or both. Thereafter, the capsid preparation comprising the viral capsids is released for sale and purchase and enters the distribution chain. The $R_1(^1H_2O)$ and/or $R_2(^1H_2O)$ constant of water can be measured by the transporter or distributor or the purchaser/user before use to confirm that the capsid preparation still comprises an acceptable amount of full viral capsids. If the measured $R_1(^1H_2O)$ and/or $R_2(^1H_2O)$ constant of the capsid preparation is outside of the reference range provided by the manufacturer, meaning that the viral capsids have an unacceptable amount of empty capsids, the specific vial can be rejected. A rejected vial should be removed from the distribution chain and not used.

In addition to the surprising discovery that solvent NMR, e.g., water NMR, can be used to detect if viral capsids are full or empty, the present inventors have also surprisingly discovered that the capsid content (i.e., the percent of full capsids based on the total amount of capsids in a sample) can be quantified using solvent NMR as well. The manufacturer as well as transporters, distributors, commercial end users, and researchers can use solvent NMR to noninvasively inspect the capsid preparations to ensure that the viral capsids are full, or have a capsid content above a predetermined capsid content minimum. This is particularly relevant in a research setting.

In addition to being noninvasive, additional advantages of low field solvent NMR includes low cost instrumentation (e.g., a desktop or handheld NMR), simple and rapid data acquisition and analysis, and minimal technical expertise requirement whereby the results are readily available within <1 min. It should be appreciated that the measurements can occur destructively as well, whereby the vial is opened, if needed. Further, the method described herein can utilize high field NMR, if needed.

In practice, the manufacturer can provide the acceptable $R_2(^1H_2O)$ or $R_1(^1H_2O)$ range in $sec^{-1}$, e.g., a control or reference range, for the capsid preparation comprising the viral capsids at some temperature. There is evidence that raising the temperature of capsid preparations to room temperature is not harmful, therefore the NMR relaxation times or rates of solvent for the capsid preparations can be measured in a range from about −20° C. to about 30° C., provided the sample remains a liquid below 0° C. The user will then measure the $R_2(^1H_2O)$ or $R_1(^1H_2O)$ of the capsid preparation comprising the viral capsids at the same temperature and magnetic field strength and compare the measured $R_2(^1H_2O)$ or $R_1(^1H_2O)$ value with the manufacturer-specified acceptable range of $R_2(^1H_2O)$ or $R_1(^1H_2O)$, i.e., reference, as understood by the person skilled in the art, to determine if the capsid preparation comprising the viral capsids is safe to use (i.e., comprises full viral capsids or an acceptable capsid content). Acceptable capsid content, i.e., percent of full capsids based on the total amount of capsids in a sample, typically are greater than about 50%, preferably greater than about 80%, even more preferably greater than about 90% and can include values greater than about 95%, greater than about 98%, greater than about 99%, and greater than about 99.5%.

Accordingly, in a first aspect, a method of determining if a capsid preparation comprises full or empty viral capsids is described, said method comprising: measuring the transverse relaxation rate of solvent $R_{2,m}$ in the capsid preparation; and determining if the capsid preparation comprises full and/or empty viral capsids by comparing the measured $R_{2,m}$ to reference transverse relaxation rates of solvent $R_{2,r}$, wherein the full viral capsids and the empty viral capsids each have a unique reference $R_{2,r}$ value. The transverse relaxation rate of solvent $R_2$ can be determined using solvent NMR, preferably low field solvent NMR. The measuring of the transverse relaxation rate of solvent $R_2$ in the capsid preparation in a vial can be done non-invasively. The reference $R_{2,r}$ values for the full capsids and the empty capsids, at a specified temperature and magnetic field strength, can be measured by the manufacturer and the result listed in the package insert and/or the vial of the capsid preparation. In one embodiment, $R_{2,m}$ is measured at substantially the same temperature as $R_{2,r}$. Preferably the solvent is water. In one embodiment, the vial comprising the capsid preparation that is measured ($R_{2,m}$) is substantially identical to the vial comprising the capsid preparation that is the reference ($R_{2,r}$). The distributor or purchaser/administrator can then use NMR, e.g., benchtop or handheld, to measure $R_{2,m}$ at the specified temperature and magnetic field strength and compare it with the reference $R_{2,r}$ range listed in the package insert or vial before distribution or usage. If the measured $R_{2,m}$ is the same, or substantially the same, for example within a range provided by the manufacturer or regulator for the specific preparation, as the reference $R_{2,r}$ value for full capsids, the capsid preparation comprises full viral capsids, and as such can be distributed or used.

It should be appreciated that the method of the first aspect can be based on the water proton transverse relaxation time $T_2$, instead of the rate $R_2$, as readily determined by the person skilled in the art. In other words, when water is the solvent, the manufacturer provides $T_2(^1H_2O)$ reference values for the full capsids and the empty capsids and the measured $T_2(^1H_2O)$ of the capsid preparation is compared to the $T_2(^1H_2O)$ reference values for the full capsids and the empty capsids. The transverse relaxation time $T_2(^1H_2O)$ ($=1/R_2(^1H_2O)$) value can be extracted by fitting experimental data to Formula (1):

$$I(t) = I_0 \times \exp(-t/T_2(^1H_2O)) \tag{1}$$

where I(t) is the $^1H_2O$ signal intensity at time t, $I_0$ is the initial $^1H_2O$ signal intensity when t=0, and t is the $T_2(^1H_2O)$ delay time.

In a second aspect, a method of determining if a capsid preparation comprises full or empty viral capsids is described, said method comprising: measuring the longitudinal relaxation rate of solvent $R_{1,m}$ in the capsid preparation; and determining if the capsid preparation comprises full and/or empty viral capsids by comparing the measured $R_{1,m}$ to reference longitudinal relaxation rates of solvent $R_{1,r}$, wherein the full viral capsids and the empty viral capsids each have a unique reference $R_{1,r}$ value. The longitudinal relaxation rate of solvent $R_1$ can be determined using solvent NMR, preferably low field solvent NMR. The measuring of the longitudinal relaxation rate of solvent $R_1$ in the capsid preparation can be done non-invasively in a vial. The reference $R_{1,r}$ values for the full capsids and the empty capsids, at a specified temperature and magnetic field strength, can be measured by the manufacturer and the result listed in the package insert and/or the vial of the capsid preparation. In one embodiment, $R_{1,m}$ is measured at substantially the same temperature as $R_{1,r}$. Preferably the solvent is water. In one embodiment, the vial comprising the capsid preparation that is measured ($R_{1,m}$) is substantially identical to the vial comprising the capsid preparation that is the reference ($R_{1,r}$). The distributor or purchaser/administrator can then use NMR, e.g., benchtop or handheld, to measure $R_{1,m}$ at the specified temperature and magnetic field strength and compare it with the reference $R_{1,r}$ range listed in the package insert or vial before distribution or usage. If the measured $R_{1,m}$ is the same, or substantially the same, as the reference $R_{1,r}$ value for full capsids, the capsid preparation comprises full viral capsids, and as such can be distributed or used.

It should be appreciated that the method of the second aspect can be based on the water proton longitudinal relaxation time $T_1$, instead of the rate $R_1$, as readily determined by the person skilled in the art. In other words, when water is the solvent, the manufacturer provides $T_1(^1H_2O)$ reference values for the full capsids and the empty capsids and the measured $T_1(^1H_2O)$ of the capsid preparation is compared to the $T_1(^1H_2O)$ reference values for the full capsids and the empty capsids. The longitudinal relaxation time $T_1(^1H_2O)$ $(=1/R_1(^1H_2O))$ can be extracted by fitting experimental data to Formula (2) if the inversion recovery pulse sequence was used:

$$I(t)=I_0 \times [1-2*\exp(-t/T_1(^1H_2O))] \qquad (2)$$

or by fitting experimental data to Formula (3) if the saturation recovery pulse sequence was used:

$$I(t)=I_0 \times [1-\exp(-t/T_1(^1H_2O))] \qquad (3)$$

where $I(t)$ is the $^1H_2O$ signal intensity at time t, $I_0$ is the $^1H_2O$ signal intensity when the signal is fully recovered, and t is the $T_1(^1H_2O)$ recovery time. The person skilled in the art will readily determine the situations where one of the above listed pulse sequences could be beneficially used to extract reliable values of $T_1(^1H_2O)$.

In a third aspect, a method of determining a capsid content of a capsid preparation is described, said method comprising measuring the relaxation rate of solvent $R_{2,m}$ or $R_{1,m}$ in the capsid preparation, and calculating the capsid content of the capsid preparation from a standard calibration curve created using the $R_2$ or $R_1$ of solvent, e.g., water, relative to known capsid contents for said capsid preparation. In practice, the manufacturer can provide the calibration curve of relaxation rate $R_1$ or $R_2$ versus the known capsid content (e.g., percent of full capsids based on the total amount of capsids in the sample) measured at a given temperature (e.g., 25° C.). The calibration curve can be provided in the form of a plot, a table, an equation, or, if linear, slope plus intercept. The user will then measure the solvent $R_{1,m}$ or $R_{2,m}$ of the capsid preparation at the same temperature and use the calibration curve to determine the capsid content, as understood by the person skilled in the art. The manufacturer can also provide a "minimum acceptable capsid content" for the capsid preparation, whereby below the minimum acceptable capsid content the preparation should not be released, distributed or used. It should be appreciated that the standard calibration curve/table can be prepared by the user, if necessary, and that the minimum acceptable capsid content may vary depending on the capsid used and/or the identification and/or concentration of the vector genome contained therein. Preferably the solvent is water.

In one embodiment of the third aspect, a method of determining a capsid content of a capsid preparation comprises is described, said method comprising: measuring the transverse relaxation rate of solvent $R_{2,m}$ in the capsid preparation; and calculating the capsid content of the preparation from a standard calibration curve created using the $R_2$ of solvent relative to the known capsid content for said preparation. The transverse relaxation rate of solvent $R_2$ can be determined using solvent NMR, preferably low field solvent NMR. The measuring of the transverse relaxation rate of solvent $R_2$ in the capsid preparation can be done non-invasively in a vial. In one embodiment, $R_{2,m}$ is measured at substantially the same temperature as the temperature of the calibration curve. In one embodiment, the vial comprising the capsid preparation that is measured ($R_{2,m}$) is substantially identical to the vial comprising the capsid preparation that is the reference ($R_{2,r}$). The distributor or purchaser/administrator can then use NMR, e.g., benchtop or handheld, to measure $R_{2,m}$ at the specified temperature and magnetic field strength and determine the capsid content from the information provided about the calibration curve, as readily understood by the person skilled in the art. If the capsid content is above some predetermined minimum acceptable capsid content, as provided by the manufacturer, the capsid preparation can be distributed or used. Preferably the solvent is water.

In another embodiment of the third aspect, a method of determining a capsid content of a capsid preparation comprises is described, said method comprising: measuring the longitudinal relaxation rate of solvent $R_{1,m}$ in the capsid preparation; and calculating the capsid content of the preparation from a standard calibration curve created using the $R_1$ of solvent relative to the known capsid content for said preparation. The longitudinal relaxation rate of solvent $R_1$ can be determined using solvent NMR, preferably low field solvent NMR. The measuring of the longitudinal relaxation rate of solvent $R_1$ in the capsid preparation can be done non-invasively in a vial. In one embodiment, $R_{1,m}$ is measured at substantially the same temperature as the temperature of the calibration curve. In one embodiment, the vial comprising the capsid preparation that is measured ($R_{1,m}$) is substantially identical to the vial comprising the capsid preparation that is the reference ($R_{1,r}$). The distributor or purchaser/administrator can then use NMR, e.g., benchtop or handheld, to measure $R_{1,m}$ at the specified temperature and magnetic field strength and determine the capsid content from the information provided about the calibration curve, as readily understood by the person skilled in the art. If the capsid content is above some predetermined minimum acceptable capsid content, as provided by the manufacturer, the capsid preparation can be distributed or used. Preferably the solvent is water.

It should be appreciated that the method of the third aspect can be based on the relaxation time of solvent, e.g., $T_2$ or $T_1$, instead of the rate, as readily determined by the person skilled in the art. In other words, the manufacturer provides a calibration curve created using the measured $T_2$ or $T_1$ of solvent relative to the known capsid content for said preparation. Preferably, the solvent is water.

In a fourth aspect, a method of preparing the standard calibration curve for a capsid content is described, said method comprising:

obtaining a sample of empty viral capsids and a sample of full viral capsids, wherein the full viral capsids comprise a vector genome and wherein the empty viral capsids are substantially devoid of said vector genome, and wherein the empty and full capsids comprise identical capsomeres;

optionally producing at least one or more mixed samples having a percent of full to empty viral capsids between 0% and 100%, wherein said one or more samples are obtained by mixing x parts of empty viral capsids with (100−x) parts of full viral capsids;

measuring the relaxation rate of solvent, $R_2$ or $R_1$, of the sample of the empty viral capsids, the full viral capsids, and the optional at least one mixed sample;

plotting the percent concentration of full to empty viral capsids to the relaxation rate of solvent and determining the best-fit regression line.

The best-fit regression line can be used to determine the percent of full to empty capsids of an unknown sample based on the measured relaxation rate of solvent of said unknown sample, as readily understood by the person skilled in the art. As will be discussed hereinbelow, it may be possible to create a calibration curve with just two data points (e.g., if $R_2(^1H_2O)$ versus full capsid % is linear), however, it is contemplated that three, four, five, six, seven, eight, or more data points may be necessary depending on the nature of the viral capsid and the vector genome contained therein. It should be appreciated that the calibration curve is not required to be linear. As long as a relationship between $R_2$ or $R_1$ and full capsid percent is monotonous, an unknown percent can be calculated using a $R_{2,m}$ or $R_{1,m}$. It should be appreciated that the relaxation rate of solvent can be the transverse ($R_2$) or the longitudinal ($R_1$) relaxation rate. It should be appreciated that the method of the fourth aspect can be based on the relaxation time $T_2$ or $T_1$, instead of the rate, as readily determined by the person skilled in the art. For example, $T_2(^1H_2O)$, or more precisely $T_2(^1H_2O)^*$ (apparent $T_2(^1H_2O)$), can be estimated from the signal width, such as the width of the $^1H_2O$ peak. Preferably, the solvent is water.

The present inventors have thus disclosed a nondestructive quality control technology using solvent NMR to determine if the viral capsids in capsid preparations are full or empty, or some percentage in between, with the understanding that capsid preparations having an unacceptable percentage of empty capsids should be removed from the distribution stream because they may have a reduced potency and/or may be dangerous to a patient. The method described herein allows for the manufacturer and/or distributor and/or end user to monitor the percent of full capsids in the capsid preparations during transport and/or storage. This can be done without opening the vial or peeling off the label. The accuracy of the capsid content is within about ±10% of the actual capsid content, preferably within about ±5%, even more preferably within about ±3%, and most preferably within about ±1%. These advantages over existing analytical techniques can significantly tighten the quality assurance of capsid preparations, thereby improving therapy safety and outcome and reducing therapy variability. It will also save costs because the sample is not consumed or perturbed in any fashion and can still be used for other purposes, such as patient treatment.

In a fifth aspect, the method described herein can also be used to assess the stability of preparation noninvasively. This is achieved by monitoring a vial comprising a capsid preparation over time, with or without stress-induced damage including, but not limited to, temperature excursions, freeze/thaw, and agitation, and observe any changes in $R_1(^1H_2O)$ or $R_2(^1H_2O)$. If the change exceeds an allowable range, as identified by the manufacturer or FDA regulator, then the capsid preparation should not be used or distributed.

Accordingly, one embodiment of the fifth aspect relates to a method of determining if a capsid preparation has experienced stress-induced damage selected from the group consisting of temperature excursions, a freeze/thaw process, light, and agitation, said method comprising:
measuring the transverse relaxation rate of solvent $R_{2,m}$ in the capsid preparation; and
determining if the capsid preparation has experienced stress-induced damage by comparing the measured $R_{2,m}$ to a reference transverse relaxation rate of solvent $R_{2,r}$, wherein the reference $R_{2,r}$ represents an acceptable range for the capsid preparations,
wherein when the measured $R_{2,m}$ is inside the reference $R_{2,r}$ range, the capsid preparation has not experienced substantial stress-induced damage and can be used or distributed.

Preferably, the solvent is water.

Another embodiment of the fifth aspect relates to a method of determining if a capsid preparation has experienced stress-induced damage selected from the group consisting of temperature excursions, a freeze/thaw process, light, and agitation, said method comprising:
measuring the longitudinal relaxation rate of solvent $R_{1,m}$ in the capsid preparation; and
determining if the capsid preparation has experienced stress-induced damage by comparing the measured $R_{1,m}$ to a reference longitudinal relaxation rate of solvent $R_{1,r}$, wherein the reference $R_{1,r}$ represents an acceptable range for the capsid preparations,
wherein when the measured $R_{1,m}$ is inside the reference $R_{1,r}$ range, the capsid preparation has not experienced substantial stress-induced damage and can be used or distributed.

Preferably, the solvent is water.

It should be appreciated that the method of the fifth aspect can be based on the relaxation time of solvent, e.g., $T_2$ or $T_1$, instead of the rate, as readily determined by the person skilled in the art. In other words, the manufacturer provides the reference $T_{2,r}$ or $T_{1,r}$ of solvent, or range, which is considered an acceptable range for the capsid preparations. Preferably, the solvent is water.

In a sixth aspect, the method described herein enables the non-destructive assessment of shell/core structures Y (e.g., protein, LNP or polymer) that can encapsulate material X (e.g., nucleic acids such as DNA or RNA) inside the shell, formulated as aqueous suspensions, without opening the vial or preparation container, without adding any additives, without peeling off the label on the vial, and without relying on sedimentation principles (e.g., AUC).

In one embodiment of the sixth aspect, a method of determining if a shell preparation comprises full or empty shells is described, wherein the shell preparation comprises shell/core structures Y that encapsulate the material X, wherein Y=capsid protein, LNP, or a polymer and X=a nucleic acid (e.g., DNA or RNA), said method comprising:
measuring the transverse relaxation rate of solvent $R_{2,m}$ in the shell preparation; and determining if the shells in the shell preparation are full or empty by comparing the measured $R_{2,m}$ to reference transverse relaxation rates of solvent $R_{2,r}$, wherein the full shells and the empty shells each have a unique reference $R_{2,r}$ value. The transverse relaxation rate of solvent $R_2$ can be determined using solvent NMR, preferably low field solvent NMR. The measuring of the transverse relaxation rate of solvent $R_2$ in the shell preparation in a vial can be done non-invasively. The reference $R_{2,r}$ values for the full shells and the empty shells, at a specified temperature and magnetic field strength, can be measured by the manufacturer and the result listed in the package insert and/or the vial of the shell preparation. In one embodiment, $R_2$ in is measured at substantially the same temperature as $R_{2,m}$. Preferably, the solvent is water. In one embodiment, the vial comprising the shell preparation that is measured ($R_{2,m}$) is substantially identical to the vial comprising the shell preparation that is the reference ($R_{2,r}$). The distributor or purchaser/administrator can then use NMR, e.g., benchtop or handheld, to measure $R_{2,m}$ at the specified temperature and magnetic field strength and compare it with the reference $R_{2,r}$ range listed in the package insert or vial before distribution or usage. If the measured $R_{2,m}$ is the same, or substantially the same, for example within a range provided by the manufacturer or regulator for the specific preparation, as the reference $R_{2,r}$ value for full shells, the shell preparation comprises full shells of material X, and as such can be distributed or used.

In one embodiment of the sixth aspect, a method of determining if a shell preparation comprises full or empty shells is described, wherein the shell preparation comprises shell/core structures Y that encapsulate the material X, wherein Y=capsid protein, LNP, or a polymer and X=a nucleic acid (e.g., DNA or RNA), said method comprising:
measuring the longitudinal relaxation rate of solvent $R_{1,m}$ in the shell preparation; and determining if the shells in the shell preparation are full or empty by comparing the measured $R_{1,m}$ to reference longitudinal relaxation rates of solvent $R_{1,r}$, wherein the full shells and the empty shells each have a unique reference $R_{1,r}$ value. The longitudinal relaxation rate of solvent $R_1$ can be determined using solvent NMR, preferably low field solvent NMR. The measuring of the longitudinal relaxation rate of solvent $R_1$ in the shell preparation in a vial can be done non-invasively. The reference $R_{1,r}$ values for the full shells and the empty shells, at a specified temperature and magnetic field strength, can be measured by the manufacturer and the result listed in the package insert and/or the vial of the shell preparation. In one embodiment, $R_{1,m}$ is measured at substantially the same temperature as $R_{1,r}$. Preferably, the solvent is water. In one embodiment, the vial comprising the shell preparation that is measured ($R_{1,m}$) is substantially identical to the vial comprising the shell preparation that is the reference ($R_{1,r}$). The distributor or purchaser/administrator can then use NMR, e.g., benchtop or handheld, to measure $R_{1,m}$ at the specified temperature and magnetic field strength and compare it with the reference $R_{1,r}$ range listed in the package insert or vial before distribution or usage. If the measured $R_{1,m}$ is the same, or substantially the same, for example within a range provided by the manufacturer or regulator for the specific preparation, as the reference $R_{1,r}$ value for full shells, the shell preparation comprises full shells of material X, and as such can be distributed or used.

It should be appreciated that the methods of the sixth aspect can be based on the relaxation time of solvent, e.g., $T_2$ or $T_1$, instead of the rate, as readily determined by the person skilled in the art. In other words, when water is the solvent, the manufacturer provides $T_2(^1H_2O)$ or $T_1(^1H_2O)$ reference values for the full shells and the empty shells and the measured $T_2(^1H_2O)$ or $T_1(^1H_2O)$ of the shell preparation is compared to the $T_2(^1H_2O)$ or $T_1(^1H_2O)$ reference values for the full shells and the empty shells.

In a seventh aspect, a method of determining the percent of full shells in a shell preparation is described, said method comprising measuring the relaxation rate of solvent $R_{2,m}$ or $R_{1,m}$ in the shell preparation, and calculating the percent of full shells in the shell preparation from a standard calibration curve created using the $R_2$ or $R_1$ of solvent, e.g., water, relative to known percentages of full shells for a shell preparation. In practice, the manufacturer can provide the calibration curve of relaxation rate $R_1$ or $R_2$ versus the known percentages of full shells for a shell preparation (i.e., percent of full shells based on the total amount of shells in the sample) measured at a given temperature (e.g., 25° C.). The calibration curve can be provided in the form of a plot, a table, an equation, or, if linear, slope plus intercept. The user will then measure the solvent $R_{1,m}$ or $R_{2,m}$ of the shell preparation at the same temperature and use the calibration curve to determine the percent of full shells in the shell preparation, as understood by the person skilled in the art. The manufacturer can also provide a minimum acceptable percent of shells that are full for the shell preparation, whereby below the minimum acceptable percent, the shell preparation should not be released, distributed or used. It should be appreciated that the standard calibration curve/table can be prepared by the user, if necessary, and that the minimum acceptable percent of full shells in a shell preparation may vary depending on the nature of the shell preparation. Preferably the solvent is water.

It should be appreciated that the method of the seventh aspect can be based on the relaxation time of solvent, e.g., $T_2$ or $T_1$, instead of the rate, as readily determined by the person skilled in the art. In other words, the manufacturer provides a calibration curve created using the measured $T_2$ or $T_1$ of solvent relative to the known percent of full shells for said preparation. Preferably, the solvent is water.

In an eight aspect, the method described herein can also be used to assess the stability of a shell preparation noninvasively. This is achieved by monitoring a vial comprising the shell preparation over time, with or without stress-induced damage including, but not limited to, temperature excursions, freeze/thaw, and agitation, and observe any changes in $R_1(^1H_2O)$ or $R_2(^1H_2O)$. If the change exceeds an allowable range, as identified by the manufacturer or FDA regulator, then the shell preparation should not be used or distributed.

In one embodiment of the eighth aspect, a method of determining if a shell preparation has experienced stress-induced damage selected from the group consisting of temperature excursions, a freeze/thaw process, light, and agitation is described, wherein the shell preparation comprises shell/core structures Y that encapsulate the material X, wherein Y=capsid protein, LNP, or a polymer and X=a nucleic acid (e.g., DNA or RNA), said method comprising:
  measuring the transverse relaxation rate of solvent $R_{2,m}$ in the shell preparation; and
  determining if the shell preparation has experienced stress-induced damage by comparing the measured $R_{2,m}$ to a reference transverse relaxation rate of solvent $R_{2,r}$, wherein the reference $R_{2,r}$ represents an acceptable range for the shell preparation,
  wherein when the measured $R_{2,m}$ is inside the reference $R_{2,r}$ range, the shell preparation has not experienced substantial stress-induced damage and can be used or distributed.

Preferably, the solvent is water.

In one embodiment of the eighth aspect, a method of determining if a shell preparation has experienced stress-induced damage selected from the group consisting of temperature excursions, a freeze/thaw process, light, and agitation is described, wherein the shell preparation comprises shell/core structures Y that encapsulate the material X, wherein Y=capsid protein, LNP, or a polymer and X=a nucleic acid (e.g., DNA or RNA), said method comprising:
  measuring the longitudinal relaxation rate of solvent $R_{1,m}$ in the shell preparation; and
  determining if the shell preparation has experienced stress-induced damage by comparing the measured $R_{1,m}$ to a reference longitudinal relaxation rate of solvent $R_{1,r}$, wherein the reference $R_{1,r}$ represents an acceptable range for the shell preparation,
  wherein when the measured $R_{1,m}$ is inside the reference $R_{1,r}$ range, the shell preparation has not experienced substantial stress-induced damage and can be used or distributed.

Preferably, the solvent is water.

It should be appreciated that the methods of the eighth aspect can be based on the relaxation time of solvent, e.g., $T_2$ or $T_1$, instead of the rate, as readily determined by the person skilled in the art. In other words, the manufacturer provides the reference $T_{2,r}$ or $T_{1,r}$ of solvent, or range, which is considered an acceptable range for the shell preparations. Preferably, the solvent is water.

The features and advantages of the invention are more fully shown by the illustrative examples discussed below.

EXAMPLE 1

Figure 3A:
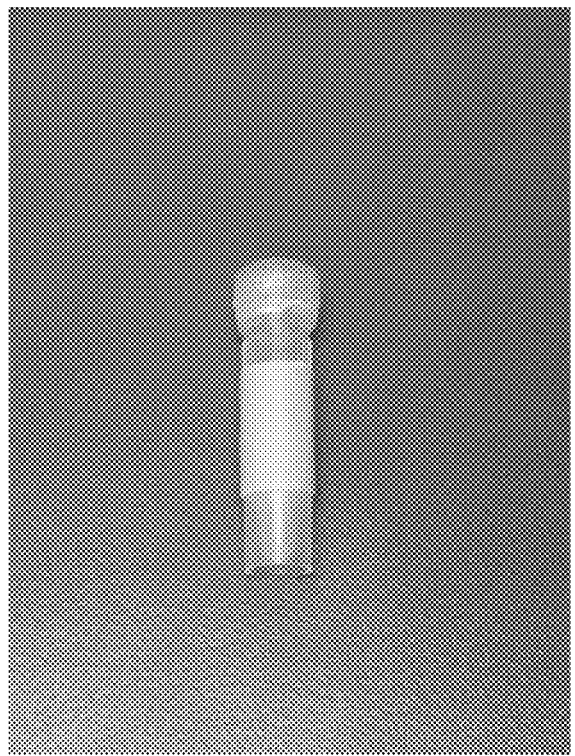
FIG. 3A illustrates a sealed and labelled plastic vial containing capsid solution.
Figure 3B:
FIG. 3B illustrates the sealed vial of FIG. 3A being inserted into the benchtop NMR instrument for measurement.

The capability of $R_2(^1H_2O)$ to detect the differences between full and empty AAV9 capsids was explored. Two identical samples of the filled capsids (AVV9-CMV-C1FP-1 and AVV9-CMV-GFP-2) and one sample of the empty capsids (AVV9-Empty) were analyzed. An example of the sample vial is shown in FIGS. 3A and 3B, wherein the sample vial is a plastic container with a plastic cap. The samples AAV9-CMV-GFP-1 and AVV9-CIV-GFP-2 contain full capsids with the transgene that has inverted terminal repeats (ITRs) with cytomegalovirus green fluorescent protein cassette in them (500 μL each, 2.40×10$^{13}$ vg/mL in 1×PBS buffer containing 0.001% Plutonic F-68, 100 mM sodium citrate, and 0.22 mm filter sterilized) and the sample AAV9-Empty is an empty capsid without any transgene (500 μL each, 2.01×10$^{13}$ vg/ml, in 1×PBS buffer containing 0.001% Pluronic F-68, 100 mM sodium citrate, and 0.22 mm filter sterilized).

Water proton relaxation of each sample was measured at 0.56 T (23.8 MHz $^1$H resonance frequency, Oxford Instruments MQC+ equipped with a PRO 1193 probe) noninvasively, in the original vials without opening and/or aliquoting the sample. To measure the water proton transverse relaxation time $T_2(^1H_2O)$, Carr-Purcell-Meiboom-Gill (CPMG) experiments were used. The person skilled in the art would understand that other methods and NMR instruments can be used to determine $T_2(^1H_2O)$, and the CPMG pulse sequence used herein is not intended to limit the determination of $T_2(^1H_2O)$.

Water proton transverse relaxation time $T_2(^1H_2O)$ measured using CPMG pulse sequence was extracted by fitting experimental echo decay data to Formula (1):

$$I(t) = I_0 \times \exp(-t/T_2(^1H_2O)) \quad (1)$$

where I(t) is the water proton echo signal intensity at time t, $I_0$ is the initial water proton echo signal at t=0, and t is the echo delay time. Measurement parameters included relaxation delay of 15 sec, interpulse delay of 500 μsec, and 20,000 echoes were collected with 4 accumulated transients. The data collection time is ca. 2 min. Note that the number of transients can be reduced to 1 if the volume of the sample is 1 mL or higher. This would cut the data collection time by approximately half. Extracted water proton relaxation time $T_2(^1H_2O)$ values were converted to water proton relaxation rate $R_2(^1H_2O)$ using Formula (2):

$$R_2(^1H_2O) = 1/T_2(^1H_2O) \quad (2)$$

Table 1 shows water proton relaxation measurements (both $T_2(^1H_2O)$ and $R_2(^1H_2O)$) of full and empty AAV9 capsid samples. These observations demonstrate significant differences in water proton relaxation parameters between full and empty AAV9 capsids. Such differences could be visually seen in FIG. 1 presenting the values of $R_2(^1H_2O)$ for full and empty capsid samples. Note that two samples of full AAV9 capsids (AAV9-CMV-GFP-1 and AVV9-CMV-GFP-2) have very similar values of water proton relaxation rate $R_2(^1H_2O)$ while the empty capsids sample (AAV9-Empty) shows a significant, more than almost 40%, increase in $R_2(^1H_2O)$.

TABLE 1

Water proton relaxation in the samples of full and empty viral capsids[a,b]

| Sample | $T_2(^1H_2O)$, sec | $R_2(^1H_2O)$, sec$^{-1}$ |
| --- | --- | --- |
| AAV9-CMV-GFP-1 | 2.300 ± 0.009 | 0.435 ± 0.002 |
| AAV9-CMV-GFP-2 | 2.317 ± 0.008 | 0.432 ± 0.002 |
| AAV9-Empty | 1.642 ± 0.008 | 0.609 ± 0.003 |

[a] The values in the Table 1 are the averages of three consecutive measurements ± SD.
[b] $T_2(^1H_2O)$, water proton transverse relaxation time, $R_2(^1H_2O)$, water proton transverse relaxation rate. The CPMG experiment measures $T_2(^1H_2O)$, which is then inverted to obtain $R_2(^1H_2O)$, i.e., $1/T_2(^1H_2O) = R_2(^1H_2O)$.

The results shown in Table 1 and FIG. 1 demonstrate that water proton relaxation rate $R_2(^1H_2O)$ can reliably distinguish full and empty AAV9 capsids. Importantly, the analysis could be done noninvasively and nondestructively, without compromising extremely valuable samples which could be further used after the measurements, such as patient treatment.

EXAMPLE 2

Of even greater importance is the potential application of $R_2(^1H_2O)$ as a tool to estimate the fraction of full capsids versus empty capsids in a given sample containing the mixture of full and empty capsids. To explore the dependence of $R_2(^1H_2O)$ on the fraction of the full AAV9 capsids, two samples containing, respectively, full and empty capsids were used. Sequential dilution of the full capsids sample (AAV9-CMV-GFP-2) with the aliquots from the empty capsids sample (AAV9-Empty) allowed to create a series of the samples containing 100%, 70%, 49%, 34%, and 0% of full AAV9 capsids. Note that such dilutions do not alter the total concentration of the AAV9 capsids which is kept at about 2×10$^{13}$ vg/mL.

Parameters of water proton relaxation were measured using the same CPMG approach as disclosed in the Example 1 herein. Measurement parameters as well as the data processing were also the same as in the Example 1 hereinabove.

Figure 2:
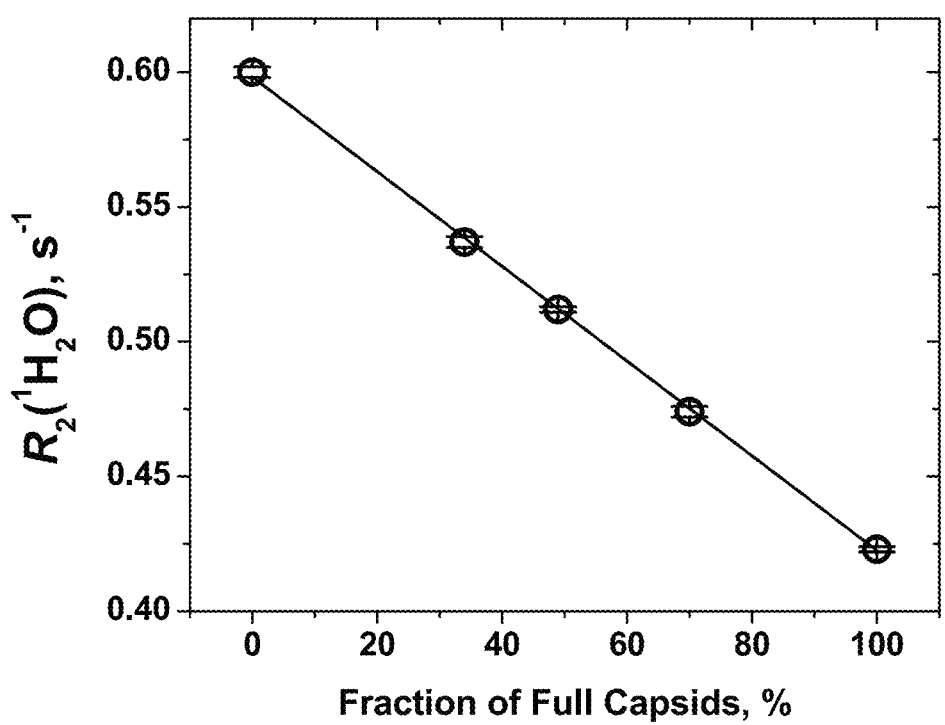
FIG. 2 presents linear dependence of water proton transverse relaxation rates, $R_2(^1H_2O)$, on the fraction of the full AAV9 capsids. Linear fit: $<r^2>=0.9997$, slope is 0.002 s$^{-1}$ per 1%; error bars (±0.001-0.002 s$^{-1}$) represent the SD of the averages of three consecutive measurements.

FIG. 2 illustrates the linear dependence of the water proton relaxation rate $R_2(^1H_2O)$ on the fraction of the full AAV9 capsids at the constant total concentration of the capsids (about 2×10$^{13}$ vg/mL). Excellent linear fit (<r$^2$>=0.9997) allows to establish a reliable correlation between the observed $R_2(^1H_2O)$ values and the fraction of the full AAV9 capsids in a given sample. The slope of the linear fit is equal to 0.002 s$^{-1}$ per 1% change of the fraction. Since the measurement error is within a range from 0.001 s$^{-1}$ to 0.002 s$^{-1}$, the present linear dependence could be advantageously used to reliably determine the fraction of the full AAV9 capsids with the accuracy from about ±3% to about ±5%.

It should be appreciated by the person skilled in the art that the slope and error parameters inter alia depend on the total concentration of the AAV9 capsids. Therefore, the determination accuracy of the fraction of the full AAV9 capsids will be different for different total capsids concentration. A person with the ordinary skill in the art will readily appreciate that the increase in total capsids concentration will result in better accuracy of the determination of the fraction of full capsids.

Linear dependence in FIG. 2 suggests that water proton relaxation rate $R_2(^1H_2O)$ provides an efficient and noninvasive tool to reliably determine the percentage of full capsids (i.e., the capsid content) in a given sample. Excellent linearity suggests that only two boundary data points (100% and 0% of full capsids) are needed for calibration purposes. Note that similar to the Example 1 hereinabove, this analysis also preserves the valuable capsid samples which can be further used after the measurements, e.g., for clinical trials or patient treatment, etc.

EXAMPLE 3

Figure 4:
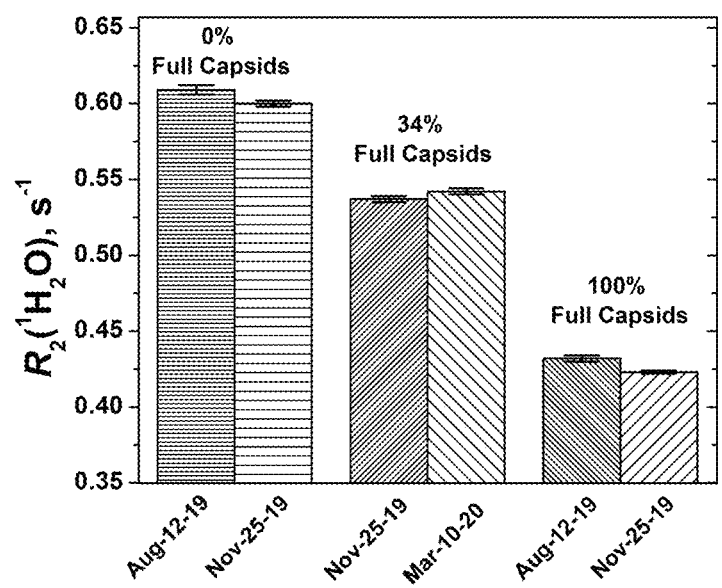
FIG. 4 illustrates the stability of capsids and the reproducibility of the measurements of water proton transverse relaxation rates, $R_2(^1H_2O)$, over time.

FIG. 4 demonstrates the stability of capsids and the reproducibility of the measurements of water proton transverse relaxation rates, $R_2(^1H_2O)$, over time. Data for the full capsids sample (AVV9-CMV-GFP-2) and for the empty capsids sample (AAV9-Empty), as well as their mixture containing 34% of full capsids, were taken within about 4 months' time span. Such longitudinal measurements over time can be used to assess the stability of the capsid preparation. Error bars (±0.001-0.002 s$^{-1}$) represent the SD of the averages of three consecutive measurements.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

What is claimed is:

1. A method of determining if a capsid preparation comprises full or empty viral capsids, said method comprising:
   measuring the transverse relaxation rate of solvent $R_{2,m}$ in the capsid preparation; and
   determining if the capsid preparation comprises full and/or empty viral capsids by comparing the measured $R_{2,m}$ to reference transverse relaxation rates of solvent $R_{2,r}$, wherein the full viral capsids and the empty viral capsids each have a unique reference $R_{2,r}$ value.

2. The method of claim 1, wherein the $R_{2,m}$ is measured using nuclear magnetic resonance (NMR).

3. The method of claim 1, wherein the $R_{2,m}$ can be measured without opening a vial containing the capsid preparation or otherwise accessing the contents of the vial containing the capsid preparation.

4. The method of claim 1, wherein the solvent is water.

5. The method of claim 1, wherein $R_{2,r}$ is provided as a range.

6. The method of claim 1, wherein $R_{2,m}$ and $R_{2,r}$ are measured at substantially the same temperature.

7. The method of claim 1, wherein $R_{2,m}$ and $R_{2,r}$ are measured at substantially the same magnetic field strength.

8. The method of claim 1, wherein the capsid preparation can be distributed or used when the measured $R_{2,m}$ is the same, or substantially the same, as the reference $R_{2,r}$ value for full capsids.

9. The method of claim 1, further comprising calculating or determining the capsid content of the preparation from a calibration curve.

10. The method of claim 9, wherein the calibration curve is created using the measured transverse relaxation rate of solvent $R_{2,m}$ relative to the known capsid content for said preparation.

11. The method of claim 9, wherein the capsid preparation can be distributed or used when the capsid content is above some predetermined minimum acceptable capsid content.

12. The method of claim 1, wherein the capsid preparation comprises viral capsids.

13. The method of claim 1, wherein the capsid preparation is contained in a vial, and wherein no additives are added to the vial prior to measurement of the transverse relaxation rate of solvent $R_{2,m}$.

14. A method of determining if a capsid preparation has experienced stress-induced damage selected from the group consisting of temperature excursions, a freeze/thaw process, light, agitation, and any combination thereof, said method comprising:
   measuring the transverse relaxation rate of solvent $R_{2,m}$ in the capsid preparation; and
   determining if the capsid preparation has experienced stress-induced damage by comparing the measured $R_{2,m}$ to a reference transverse relaxation rate of solvent $R_{2,r}$, wherein the reference $R_{2,r}$ represents an acceptable range for the capsid preparation,
   wherein when the measured $R_{2,m}$ is inside the reference $R_{2,r}$ range, the capsid preparation has not experienced substantial stress-induced damage and can be used or distributed.

15. The method of claim 14, wherein the $R_{2,m}$ is measured using nuclear magnetic resonance (NMR).

16. The method of claim 14, wherein the $R_{2,m}$ can be measured without opening a vial containing the capsid preparation or otherwise accessing the contents of the vial containing the capsid preparation.

17. The method of claim 14, wherein the solvent is water.

18. The method of claim 14, wherein $R_{2,m}$ and $R_{2,r}$ are measured at substantially the same temperature.

19. The method of claim 14, wherein $R_{2,m}$ and $R_{2,r}$ are measured at substantially the same magnetic field strength.

20. The method of claim 14, wherein the capsid preparation comprises viral capsids.

21. The method of claim 14, wherein the capsid preparation is contained in a vial, and wherein no additives are added to the vial prior to measurement of the transverse relaxation rate of solvent $R_{2,m}$.

* * * * *